United States Patent

Hoffman et al.

[11] Patent Number: 5,932,790
[45] Date of Patent: Aug. 3, 1999

[54] CLUTCH FRICTION TEST FOR MOTORCYCLE LUBRICANTS

[75] Inventors: Charles F. Hoffman, Neshanic Station; Emil J. Meny, Summit; Patrick J. Colby, Piscataway; Roger K. Nibert, Hampton, all of N.J.

[73] Assignee: Exxon Chemical Patents Inc, Linden, N.J.

[21] Appl. No.: 09/033,625

[22] Filed: Mar. 4, 1998

[51] Int. Cl.⁶ .................................................. G01N 3/56
[52] U.S. Cl. ...................................... 73/10; 73/9; 508/110
[58] Field of Search .............................. 73/9, 10, 19.11, 73/53.05; 508/110

[56] References Cited

U.S. PATENT DOCUMENTS 5,441,656 8/1995 Ohtani et al. ...................... 252/51.5 R
5,484,543 1/1996 Chandler et al. ................... 252/51.5 A

OTHER PUBLICATIONS

SAE No. 2 Clutch Friction Test Machine Test Procedure--SAE J286 NOV83.

*Primary Examiner*—Hezron Williams
*Assistant Examiner*—Thuy Vinh Tran

[57] ABSTRACT

A modified SAE No. 2 friction machine is used to evaluate the clutch friction properties of motorcycle lubricants in a process comprising measuring the torque after a break-in period at three temperature points within the ranges 30°–60° C., 70°–90° C. and 110°–150° C. over a 10 second period while the speed of the motor driving the clutch plates varies from 0–300 rpm and the clutch plate pressure is held at 50 psi.

2 Claims, 1 Drawing Sheet

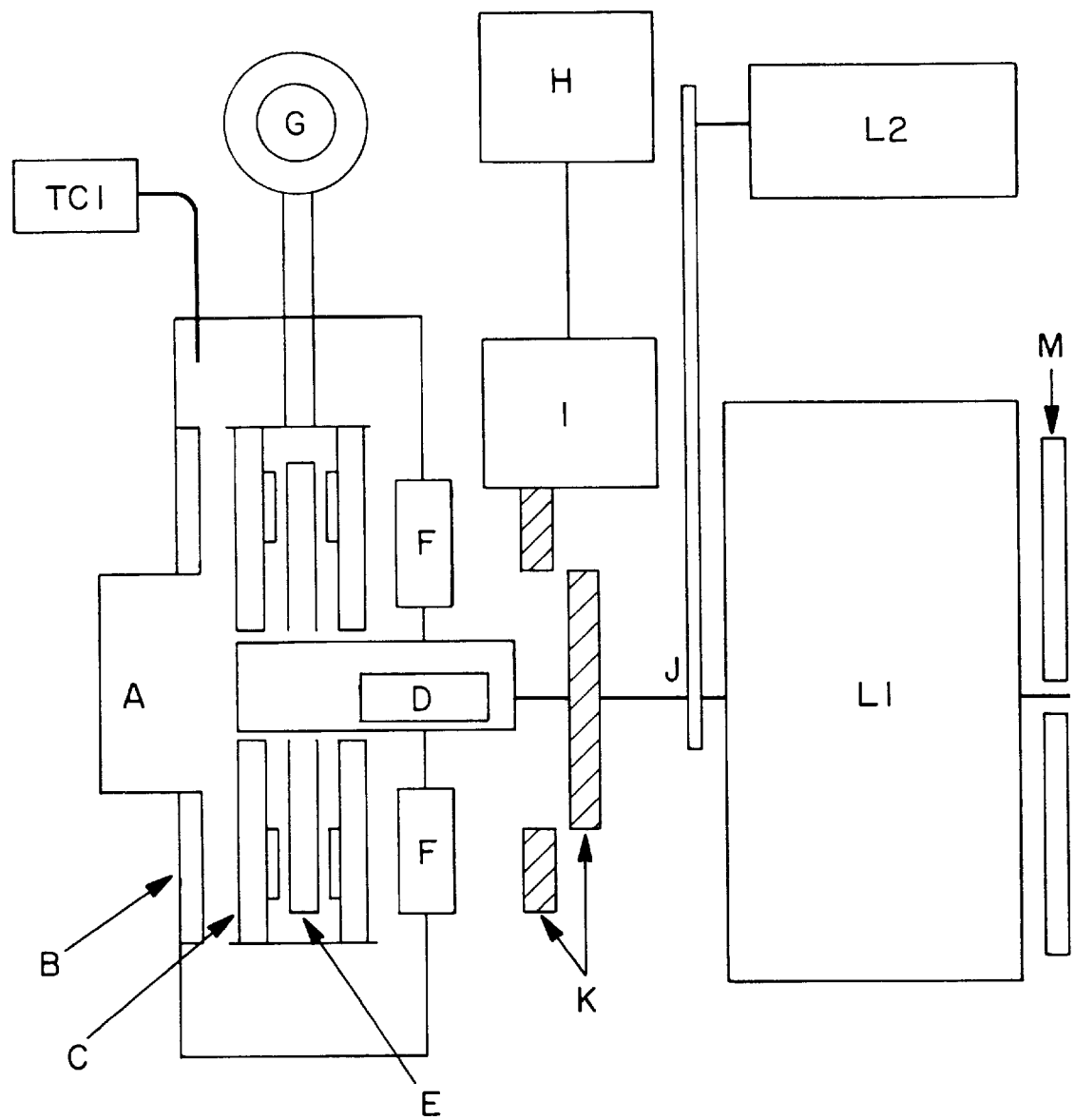

CLUTCH FRICTION TEST FOR MOTORCYCLE LUBRICANTS

This invention relates to a test procedure for evaluating the clutch friction properties of motorcycle lubricants. More particularly, this invention relates to an effective test procedure for the friction properties of such lubricants utilizing a modified SAE No. 2 friction machine.

In a typical motorcycle, a common sump lubricates the engine, transmission and wet clutch. Such universal lubricating fluids as used in motorcycles, therefore, must have a balance of both desirable friction properties and lubricity properties. Heretofore, there has been no standardized test which can effectively evaluate friction properties of motorcycle lubricants as to enable the design and formulation of such lubricants to meet requirements of manufacturers. The present invention permits one to evaluate the effect of lubricant additives on friction characteristics of motorcycle lubricants.

The SAE No. 2 machine has been used to evaluate friction properties of various fluids other than motorcycle lubricants and representative disclosures are found in U.S. Pat. No. 5,484,543, Jan. 16, 1996 to Chandler et al., U.S. Pat. No. 5,441,656, Aug. 15, 1995 to Ohtani et al. and a publication entitled "SAE No. 2 Clutch Friction Test Machine Test Procedure", published as SAE J286, November, 1983.

In accordance with the present invention there has been discovered a method for measuring the clutch friction properties of a motorcycle universal lubricant used for lubrication of the motorcycle's engine, transmission and wet clutch which comprises introducing a motorcycle lubricant test fluid into a modified SAE No. 2 test machine as shown in the Figure and measuring the coefficient of friction of the fluid according to the following procedure and conditions:

(A) stabilizing the fluid by operating the machine motor at 100 rpm, applying a pressure of 25 psi to the clutch plates and maintaining the fluid at a temperature of 30°–60° C., such as 40° C., for at least 10 minutes;

(B) while maintaining the fluid at 30°–60° C., such as 40° C., increasing the motor speed to 300 rpm over a 5 second period then decreasing the motor speed over a 5 second period to 0 rpm and continuously measuring the clutch plate speed and the torque during said 10 second period while maintaining the pressure at 50 psi;

(C) repeating step (B) twice;

(D) stabilizing the fluid at 70°–90°, such as 80° C., maintaining the motor at 100 rpm and maintaining the pressure at 50 psi for at least 10 minutes;

(E) while maintaining the fluid at 70°–90°, such as 80° C., increasing the motor speed to 300 rpm over a 5 second period then decreasing the motor speed to 0 rpm over a 5 second period and continuously measuring the clutch plate speed and the torque during said 10 second period while maintaining the pressure at 50 psi;

(F) repeating step (E) twice;

(G) stabilizing the fluid at 110°–150° C., such as 120° C., maintaining the motor speed at 100 rpm and maintaining the pressure at 50 psi for at least 10 minutes;

(H) while maintaining the fluid at 110°–150° C., such as 120° C., increasing the motor speed to 300 rpm over a 5 second period then decreasing the motor speed to 0 rpm over a 5 second period and continuously measuring the clutch plate speed and the torque during said 10 second period while maintaining the pressure at 50 psi;

(I) repeating step (H) twice;

(J) from the data of steps (C), (F) and (I), calculating the coefficient of friction at any temperature used in the preceding steps and at any clutch plate speed according to the equation $Mu=T/F \cdot N \cdot R$ where T is torque in inch-pounds, F is force applied in pounds, N is the number of active friction surfaces and R is friction plate radius in inches, said calculation being done to evaluate the operational validity of the test system and equipment;

(K) conducting a break-in period by maintaining the fluid at for 1 to 4 hours at 110°–150° C., such as 120° C., 100 rpm and 50 psi;

(L) repeating steps (H) and (I);

(M) stabilizing the fluid at 70°–90° C., such as 80° C., 100 rpm and 50 psi for at least 10 minutes;

(N) repeating steps (E) and (F);

(O) stabilizing the fluid at 30°–60° C., such as 40° C., 100 rpm and 50 psi for at least 10 minutes;

(P) repeating steps (B) and (C); and (Q) from the data of steps (L), (N) and (P), calculating the coefficient of friction for the fluid at any clutch plate speed and at any temperature according to the equation: $Mu=T/F \cdot N \cdot R$ where T is torque in inch-pounds, F is force applied in pounds, N is number of active friction surfaces and R is friction plate radius in inches, said calculation being done to evaluate the friction properties of the fluid tested.

A test procedure in accordance with this invention is carried out at temperatures preferably of 40° C., 80° C. and 120° C., but these temperatures may be expanded to ranges, respectively, of 30–60° C., 70–90° C. and 110–150° C. But the same three temperatures should be used in both phases of the test, i.e., the same three temperatures used in steps (A) through (I) should also be used in steps (K) through (P). Thus the step (K) temperature should be the same as the step (H) temperature, the step (M) temperature should be the same as the step (E) temperature and the step (O) temperature should be the same as the step (B) temperature. The coefficient of friction may be calculated for any of the three temperatures used in the series of steps comprising the test.

When data is measured over the 10 second periods referred to above, the data is continuously collected during this time period. Coefficient of friction calculations are made at any given clutch plate speed and at one of the three temperatures in the series of steps.

THE DRAWING

The FIGURE depicts schematically a modified SAE No. 2 machine which is used in accordance with this invention. The parts of the machine as labeled in the FIGURE are identified in Table I below.

TABLE I

| Legend | Part Description |
| --- | --- |
| A | Clutch pack housing |
| B | Spacer inside housing |
| C | Friction plates |
| D | Test fluid reservoir |
| E | Steel clutch plate |
| F | Air piston |
| G | Load cell for torque measurement |
| H | AC motor (static motor) 1.5 KW |
| I | Speed reducer |
| J | Motor shaft extension |
| K | Worm gear |
| L1 | 3600 rpm AC motor |
| L2 | 300 rpm AC motor and Speed Measuring Device |

TABLE I-continued

| Legend | Part Description |
|---|---|
| M | Flywheel |
| TC-1 | Thermocouple bulk fluid |

The SAE No. 2 friction machine used in this invention was fitted with adapters to accept Yamaha and Honda clutch plates. Friction and steel plates from a Yamaha XT-225 (223 cc) four stroke motorcycle were used for the lubricants tested in Table II.

The test profile consists of a pre break-in and a post break-in period. Each break-in period has three stabilizing stages at 40° C. or, more broadly, 30–60° C., 80° C. or, more broadly, 70–90° C. and 120° C. or, more broadly, 110–150° C. In between the pre and post break-in periods is a one hour break-in period at maximum test temperature of preferably 120° C. or, more broadly, 110–150° C., a maximum test pressure of 50 psi and a maximum test speed of 300 rpm. Three speed ramps from 0 to maximum test speed and back to 0 are completed at each temperature. The actual data used to determine the friction coefficient of test lubricants for the purpose of evaluating the fluid's performance is taken during the post break-in 110°–150° C. period, i.e., steps (K)–(Q). Data taken during the initial three temperature phases, the test procedure, i.e., steps (A)–(J) as recited above is for the purpose of evaluating the operational validity of the test system and is an essential part of the test procedure. Friction coefficient of the test lubricants is calculated from the measured torque values generated during this portion of the test. A friction trace is developed by plotting friction coefficient vs. clutch plate speed. By comparing the friction traces of test lubricants one is able to predict whether the lubricant will exhibit acceptable or poor clutch performance using a particular clutch material. The effect of additives on clutch performance can also be measured by comparing the test results of different oils.

Table II set forth below shows the results for three commercial lubricants which were tested in accordance with this invention. The Mu, coefficient of friction is reported below for 120° C. and a clutch plate speed of 0.4 m/second.

TABLE II

| Commercial Lubricant | Start Value | Initial Slope | Mu at 0.4 m/s | Final Slope |
|---|---|---|---|---|
| A | 0.0880 | 0.0824 | 0.0950 | −0.0120 |
| B | 0.1050 | 0.0253 | 0.1560 | −0.0070 |
| C | 0.1250 | 0.2690 | 0.1800 | 0.0090 |

Lubricant A: Honda Ultra GP Motorcycle Oil SAE 10W-40
Lubricant B: Yamalube4 4-Cycle Engine Oil SAE 10W-30
Lubricant C: 10W-30 Motorcycle oil based on "Paratemps 850" additive package, Exxon Chemical Co., Paramins Division

What is claimed is:

1. A method for measuring the clutch friction properties of a motorcycle universal lubricant used for lubrication of the motorcycle's engine, transmission and wet clutch which comprises introducing a motorcycle lubricant test fluid into a SAE No. 2 test machine as shown in the Figure and measuring the coefficient of friction of the fluid according to the following procedure and conditions:

(A) stabilizing the fluid by operating the machine motor at 100 rpm applying a pressure of 25 psi to the clutch plates and maintaining the fluid at a temperature of 30°–60° C. for at least 10 minutes;

(B) while maintaining the fluid at 30°–60° C., increasing the motor speed to 300 rpm over a 5 second period then decreasing the motor speed over a 5 second period to 0 rpm and continuously measuring the clutch plate speed and the torque during said 10 second period while maintaining the pressure at 50 psi;

(C) repeating step (B) twice;

(D) stabilizing the fluid at 70°–90° C., maintaining the motor at 100 rpm and maintaining the pressure at 50 psi for at least 10 minutes;

(E) while maintaining the fluid at 70°–90° C., increasing the motor speed to 300 rpm over a 5 second period then decreasing the motor speed to 0 rpm over a 5 second period and continuously measuring the clutch plate speed and the torque during said 10 second period while maintaining the pressure at 50 psi;

(F) repeating step (E) twice;

(G) stabilizing the fluid at 110°–150° C., maintaining the motor speed at 100 rpm and maintaining the pressure at 50 psi for at least 10 minutes;

(H) while maintaining the fluid at 110°–150° C., such as 120° C., increasing the motor speed to 300 rpm over a 5 second period then decreasing the motor speed to 0 rpm over a 5 second period and continuously measuring the clutch plate speed and the torque during said 10 second period while maintaining the pressure at 50 psi;

(I) repeating step (H) twice;

(J) from the data of steps (C), (F) and (I), calculating the coefficient of friction at any temperature used in the preceding steps and at any clutch plate speed according to the equation $Mu=T/F \cdot N \cdot R$ where T is torque in inch-pounds, F is force applied in pounds, N is the number of active friction surfaces and R is friction plate radius in inches, said calculation being done to evaluate the operational validity of the test system and equipment;

(K) conducting a break-in period by maintaining the fluid for 1 to 4 hours at 110°–150° C., 100 rpm and 50 psi;

(L) repeating steps (H) and (I);

(M) stabilizing the fluid at 70°–90° C., such as 80° C., 100 rpm and 50 psi for at least 10 minutes;

(N) repeating steps (E) and (F);

(O) stabilizing the fluid at 30°–60° C., 100 rpm and 50 psi for at least 10 minutes;

(P) repeating steps (B) and (C); and (Q) from the data of steps (L), (N) and (P), calculating the coefficient of friction for the fluid at any clutch plate speed and at any temperature used in the preceding steps according to the equation: $Mu=T/F \cdot N \cdot R$ where T is torque in inch-pounds, F is force applied in pounds, N is number of active friction surfaces and R is friction plate radius in inches, said calculation being done to evaluate the friction properties of the fluid tested.

2. The method of claim 1 wherein the temperature used in steps (A), (B) and (O) is 40° C., the temperature used in steps (D), (E) and (M) is 80° and the temperature used in steps (G), (H) and (K) is 120° C.

* * * * *